United States Patent [19]

Kimura et al.

[11] Patent Number: 4,524,351

[45] Date of Patent: Jun. 18, 1985

[54] SMOKE DETECTOR

[75] Inventors: Tetsuo Kimura; Hirofumi Fujii; Hayami Yuasa; Tatuo Yonezawa, all of Tokyo, Japan

[73] Assignee: Nittan Company, Limited, Tokyo, Japan

[21] Appl. No.: 408,050

[22] Filed: Aug. 13, 1982

[30] Foreign Application Priority Data

Aug. 20, 1981 [JP] Japan ................................ 56-129350
Feb. 2, 1982 [JP] Japan ................................. 57-14349

[51] Int. Cl.³ .............................................. G08B 17/10
[52] U.S. Cl. ..................................... 340/629; 307/356; 307/358; 340/628; 250/384
[58] Field of Search ...................... 340/628, 629, 636; 250/381, 384; 73/23, 29; 307/355, 356, 358, 362

[56] References Cited

U.S. PATENT DOCUMENTS

| | | | |
|---|---|---|---|
| 3,618,061 | 2/1971 | Livers | 73/29 |
| 3,781,692 | 12/1973 | Escoffier | 307/362 X |
| 3,823,601 | 7/1974 | Hoppesch | 73/23 |
| 3,900,785 | 8/1975 | Alric et al. | 340/636 X |
| 3,946,374 | 3/1976 | McMillian et al. | 250/381 X |
| 4,260,907 | 4/1981 | Winebarger | 307/358 X |
| 4,335,378 | 6/1982 | Coleman | 340/629 |
| 4,401,978 | 8/1983 | Solomon | 340/629 X |

Primary Examiner—James L. Rowland
Assistant Examiner—Daniel Myer
Attorney, Agent, or Firm—Murray, Whisenhunt & Ferguson

[57] ABSTRACT

In a smoke detector of the type in which smoke is detected in a detection chamber based upon a variation of an ionization current flowing therein or a variation of light beam passing therethrough, there is provided a reference signal generating section which produces a reference signal having a predetermined characteristic corresponding to typical smoke flowing into the detection chamber when a fire occurs, and a signal comparison section which compares a detection signal detected in the detection chamber with the reference signal, wherein a smoke sensing signal is produced when the detection signal is determined as a signal due to a fire but is not produced when the detection signal is determined as the signal due to the entry of an insect into the detection chamber or due to cigarette's smoke flowing thereinto.

8 Claims, 7 Drawing Figures

4,524,351

SMOKE DETECTOR

BACKGROUND OF THE INVENTION

This invention relates to a smoke detector which is effective when used as a fire detector.

A number of smoke detectors of ionization type or optical type have been manufactured. In the ionization smoke detector, a pair of electrodes across which a voltage is applied are provided in a detection chamber, and the internal atmosphere of the detection chamber is ionized by radio-active rays, so that smoke is detected from the ionization current. On the other hand, in the optical smoke detector, a light beam from a light source is introduced into a detection chamber, and a light receiving element detects the light beam which is subjected to scattering or attenuation by smoke, to thereby sense the smoke.

The smoke detectors described above frequently operate erroneously when an insect enters into the detection chamber. This will be described in more detail. In the ionization smoke detector, a pair of electrodes are provided in a reference chamber into which smoke does not substantially flow, and the internal atmosphere of the reference chamber is ionized by radio-active rays. Furthermore, a pair of electrodes are provided in a detection chamber into which smoke flows, and the internal atmosphere of the chamber is also ionized by radio-active rays. These two chambers are connected in series to each other, and the variation of the potential at the connection point is detected to sense the presence of smoke. When smoke enters into the detection chamber, the ionization current is reduced. This reduction is detected as potential variation. In general, the distance between the electrodes in the reference chamber is very small. Therefore, even a small insect can short-circuit the electrodes to abruptly change the potential, i.e., to cause the smoke detector to operate erroneously. Furthermore, when an insect sticks to the radio-active source for ionizing the internal atmosphere of the detection chamber to obstruct the ionization, the smoke detector is caused to operate erroneously.

An insect is also the largest cause for the error of the optical smoke detector, because the insect largely reflects or intercepts light.

In order to prevent the erroneous operation due to the entrance of an insect, a smoke detector has been proposed in the art in which a differentiation circuit is provided between a detection section and a signal processing section, so that a signal due to smoke is distinguished from a signal due to insect, to thereby control the signal processing section. Another smoke detector employs a method in which the signal from the detection section is supplied directly to the central monitoring section, so that it is discriminated according to the rise characteristic thereof. However, these conventional smoke detectors still suffer from problems such that the circuitry is intricate and the installation is expensive.

SUMMARY OF THE INVENTION

Accordingly, an object of this invention is to provide an improved smoke detector which does not operate erroneously when an insect enters into a detection chamber into which smoke flows but correctly and quickly operate when smoke is detected. The smoke detector of this invention has been developed on the basis of the fact that the detection chamber has a smoke entering characteristic inherent thereto, and the signal due to the entry of the insect can be discriminated according to the smoke entering characteristic, to thereby solve the aforementioned problems accompanying a conventional smoke detector.

The smoke detector in accordance with this invention includes a smoke detecting section for detecting smoke and producing a detection signal, a reference signal generating section for generating a reference signal which changes with time according to the smoke entering characteristic of the smoke detecting section, a starting section for providing a driving signal in response to the initial detection signal from the smoke detecting section 1 to start the reference signal generating section, a signal comparison section for comparing the detection signal of the smoke detecting section with the reference signal of the reference signal generating section and for providing an output when the detection signal is lower in variation than the reference signal, an integrator for integrating the output of the signal comparison section for a predetermined period of time, and a smoke sensing signal generating section for generating a smoke sensing signal when the amount of integration by the integrator reaches a predetermined value.

DETAILED DESCRIPTION OF THE PREFERRED EMBODIMENTS

Preferred embodiments of the invention will now be described with reference to the accompanying drawings.

Figure 1:
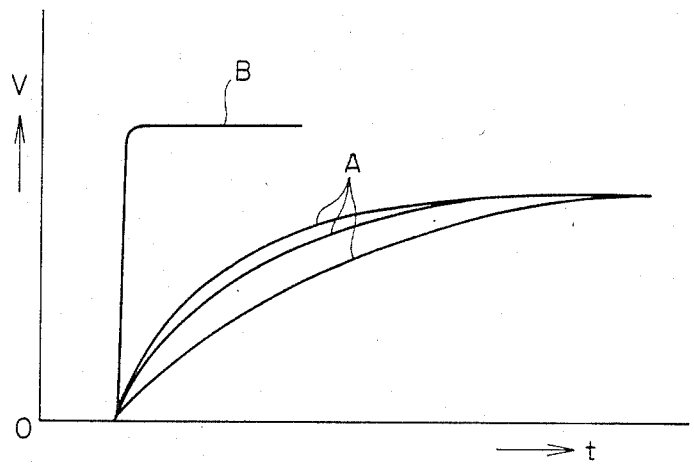
FIG. 1 is a graphical representation indicating characteristic curves for a description of smoke entering characteristics of a smoke detecting chamber.

Not only in an ionization smoke detector but also in an optical smoke detector, a detection chamber is generally provided by surrounding a smoke detecting section with a wall through which smoke can freely flow in order to eliminate unwanted noise signals, to prevent the entrance of a turbulent flow and to prevent the entrance of external light. The detection chamber thus provided serves as a kind of resistance against the flow of smoke. When a detection signal is measured with the detection chamber disposed in the atmosphere which includes smoke with a certain concentration, a curve A as shown in FIG. 1 is obtained. In the graph of FIG. 1, the horizontal axis represents time, while the vertical axis represents a detection signal (voltage). When an insect goes into the detection chamber to cause the above-described trouble, the entry of the insect appears as an abrupt change as indicated by the curve B. The curve A due to the entrance of smoke is inherently determined from the size and structure of the detection chamber. On the other hand, the entry of the insect appears as the abrupt change irrespective of the detection chamber. By utilizing this difference in characteristic, the error due to the entry of an insect can be prevented.

Figure 2A:
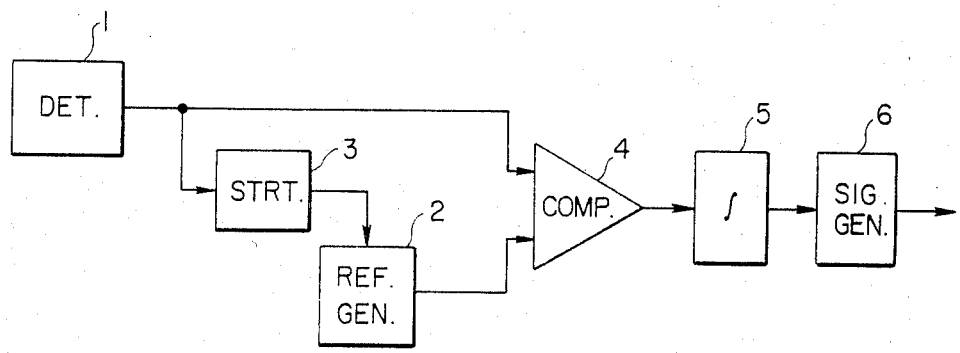
FIGS. 2A and 2B are block diagrams outlining the arrangement of smoke detectors according to first and second embodiments of this invention.

FIG. 2A is a block diagram outlining the arrangement of a smoke detector according to this invention. The smoke detector includes a smoke detecting section 1 of ionization type or optical type for detecting smoke and producing a detection signal, a reference signal generating section 2 for generating a reference signal which changes with time according to the smoke entering characteristic of the smoke detecting section 1, a starting section 3 for providing a driving signal in response to the initial detection signal from the smoke detecting section 1 to start the reference signal generating section 2, a signal comparison section 4 for comparing the detection signal of the smoke detecting section 1 with the reference signal of the reference signal generating section 2 and providing an output when the detection signal is lower in variation than the reference signal, an integrator 5 for integrating the output of the signal comparison section 4 for a predetermined period of time, and a smoke sensing signal generating section 6 for generating a smoke sensing signal when the amount of integration by the integrator 5 reaches a predetermined value.

The operation of the smoke detector thus constructed will be described with reference to FIG. 3A which illustrates voltage variations under various conditions.

Figure 3A:
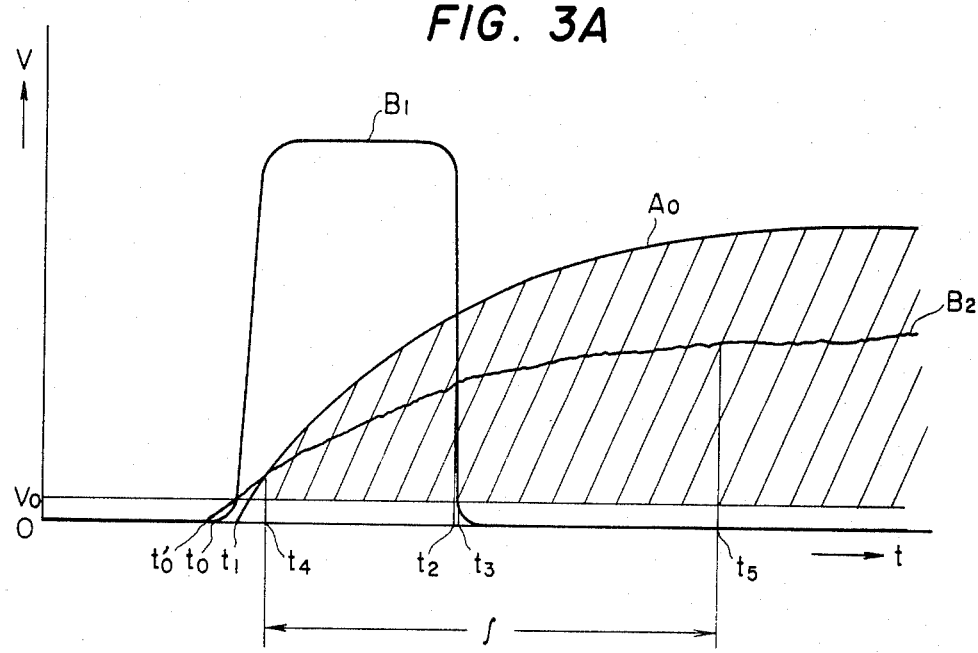
FIGS. 3A and 3B are graphical representations indicating detection signals and reference signals.

FIG. 3A is a graphical representation in which the vertical axis represents voltages and the horizontal axis represents time. For the normal period of time during which no smoke is present or no insect enters into the detection chamber, the smoke detecting section 1 outputs no detection signal and the reference signal generating section 2 generates no reference signal, or the detection signal is slightly higher than the reference signal. Accordingly, during the normal period of time, no output is provided from the signal comparison section 4.

When an insect enters into the detection chamber at the time instant $t_0$, the detection singal of the smoke detecting section 1 changes as indicated by the curve $B_1$. The starting section 3 whose operating voltage has been set to $V_0$ in order to respond to the intial detection signal of the detection section 1 is operated at the time instant $t_1$, thereby starting the reference signal generating section 2. The reference signal generating section 2 produces the reference signal which, as indicated by the curve $A_0$, rises with time according to the smoke entering characteristic in the smoke detection section 1. The reference signal $A_0$ rises substantially according to the smoke entering characteristic. Therefore, unlike the detection signal $B_1$, the reference signal $A_0$ does not rises abruptly. Thus, the detection signal $B_1$ will never be lower than the reference signal $A_0$, and therefore the signal comparison section 4 provides no output. When the insect leaves the detection chamber, the detection signal $B_1$ becomes temporarily lower than the reference signal $A_0$ between the time instants $t_2$ and $t_3$ in FIG. 3A. In this duration, the output of the signal comparison section 4 is integrated by the integrator 5. If the amount of integration of the integrator 5 is preset to a suitable value, then such a temporary output cannot reach the amount of integration thus preset, and accordingly no smoke sensing signal is produced from the smoke sensing signal generating section 6. It has been experientially confirmed that the detection signal due to the entrance of an insect is much larger than the signal due to smoke. Therefore, if the maximum value of the reference sugnal $A_0$ is set so that it will nver become higher than the detection signal which is provided in response to the entrance of the insect, then the provision of an output from the signal comparison section 4 can be prevented no matter how long an insect stays in the detection chamber.

In the case where smoke is produced at the time instant $t_0'$ and the detection signal from the smoke detecting section 1 changes gradually as indicated by the curve $B_2$, the starting section 3 is operated at the time instant $t_1$ when the detection signal exceeds the operating (threshold) voltage $V_0$ to start the reference signal generating section 2. Similar to the above-described case, the reference signal generating section 2 provides the reference signal as indicated by the curve $A_0$ which rises according to the smoke entering characteristic. Therefore, if the detection signal results from the production of smoke, its characteristic curve will never become higher than the reference signal $A_0$. In other words, the detection signal $B_2$ becomes lower than the reference signal $A_0$, for instance at the time instant $t_4$. From the time instant $t_4$, the signal comparison section 4 provides the output which, in turn, is subjected to integration in the integrator 5. When the predetermined integration value is reached at the time instant $t_5$, the integrator 5 provides the output so that the smoke sensing signal generating section 6 produces the smoke sensing signal.

Figure 4A:
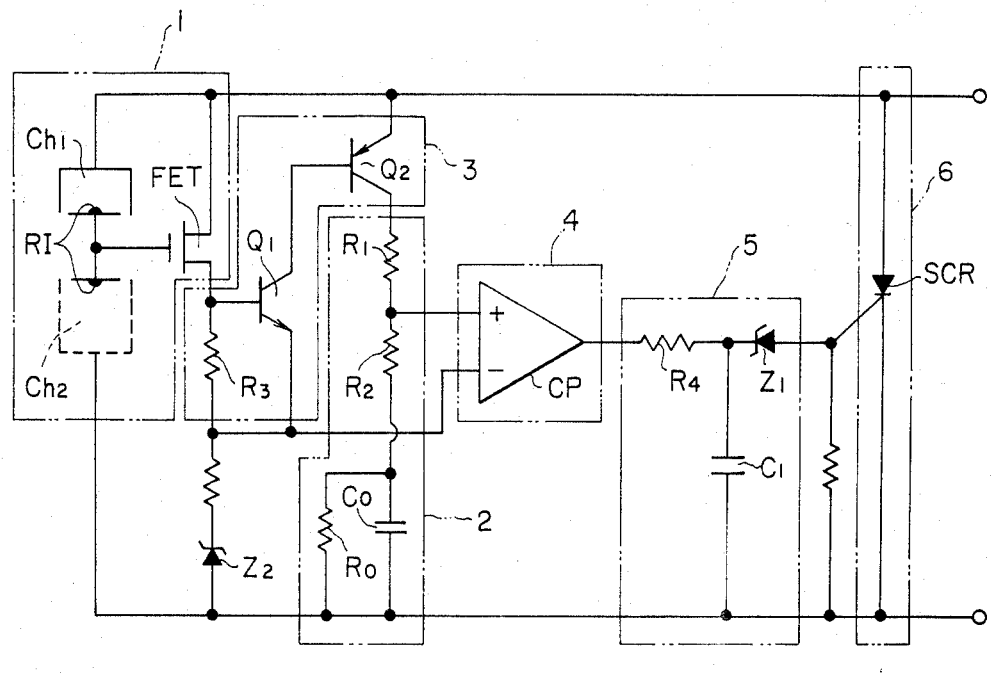
FIGS. 4A and 4B are circuit diagrams showing the smoke detector according to the first and second embodiments of the invention.

FIG. 4A shows a specific circuit diagram of the smoke detector according to the first embodiment of the invention in which an ionization smoke detecting section 1 is employed. Reference chambers $Ch_1$ and $Ch_2$, the internal atmospheres of which are ionized by radio-active sources RI, are connected in series to each other. The connection point is connected to the gate electrode of a field-effect transistor (FET) for detecting a potential variation. These chambers and the FET form the smoke detecting section 1. The reference signal generating section 2 includes a parallel circuit consisting of a capacitor $C_0$ and a resistor $R_0$, and a serial circuit of two resistors $R_1$ and $R_2$ for regulating a current flowing in the parallel circuit and for dividing a signal voltage. The starting section 3 includes a resistor $R_3$, a first transistor $Q_1$ for detecting, together with the resistor $R_3$, a current produced when the detection voltage of the smoke detecting section 1 increases, and a second transistor $Q_2$ which is controlled by the first transistor $Q_1$ to control the flow of current to be applied to the reference signal generating section 2. The signal comparison section 4 is constituted with a comparator CP, the input terminals of which are connected to the reference signal generating seciton 2 and to the detection section. The integrator 5 includes a capacitor $C_1$ for accumulating the output of the comparator CP through a resistor $R_4$, and a Zener diode $Z_1$ for detecting when the capacitor $C_1$ is charged to a predetermined value. The smoke sensing signal generating seciton 6 is consititued with a silicon controlled rectifier (SCR) which is triggered by the output of the integrator 5.

In the circuit thus arranged, for the ordinary period of time during which neither smoke is produced nor an insect enters into the detection chamber, a low voltage signal is provided at the output of the FET in the smoke detecting section 1. However, since the voltage will never exceed the Zenner voltage of the Zener diode $Z_2$ which determines the operating voltage of the stating section 3, no potential difference is developed across the resistor $R_3$ of the starting seciton 3. Therefore, the starting section 3 is not operated, and the reference signal generating section 2 is not driven. However, as the detection signal input side of the comparator CP, being applied with an ordinary level signal of the deteciton section 1, is higher than the reference signal input side of the comparator CP, the comparator CP provides no output.

When the production of smoke or the entry of an insect occurs, a detection signal or a high voltage is provided at the output of the smoke detecting section 1. This voltage is higher than the Zener voltage of the Zener diode $Z_2$, thus providing a current. Therefore, a potential difference is developed across the resistor $R_3$ in the starting section 3, so that the first transistor $Q_1$ is rendered conductive. The second transistor $Q_2$ connected to the first transistor $Q_1$ is in turn rendered conductive. Accordingly, the capacitor $C_0$ of the reference signal generating section 2 is charged at a predetermined rate through two series-connected resistors $R_1$ and $R_2$. This reference signal which increases as described above is compared with the aforementioned detection signal in the comparator CP. In the case where smoke is produced, the detection signal becomes lower than the reference signal. Therefore, the comparator CP provides the output and the capacitor $C_1$ is charged through the resistor $R_4$. When the voltage across the capacitor exceeds the Zener voltage of the Zener diode $Z_1$, a current flows in the gate electrode of the SCR. Therefore, the SCR is rendered conductive, so that the smoke sensing signal is outputted. On the other hand, in the case where the entry of an insect ocurrs, the detection signal becomes higher than the reference signal, and therefore no output is provided from the comparator CP. Accordingly, the SCR is not rendered conductive.

As is apparent from the above description, the smoke detector of the invention is simple in arrangement, and the detection signal due to the entry of smoke and the steep false detection signal due to the entry of an insect can be discriminated according to the smoke flowing characteristics of the detection chambers. Therefore, a smoke detector low in manufacturing cost and high in performance can be provided according to the invention. The first embodiment as described is advantageous in that the erroneous operation due to the abrupt signal variation attributing to the entry of an insect can be effectively eliminated. However, it is still disadvantageous in that the operation is effected for all the signal variations which are lower than the reference signal $A_0$. In other words, the operation is effected for the smoke such as from a cigarette which is much lower in concentration than smoke from a fire, as indicated by curve $B_3$ in FIG. 3B.

Figure 3B:
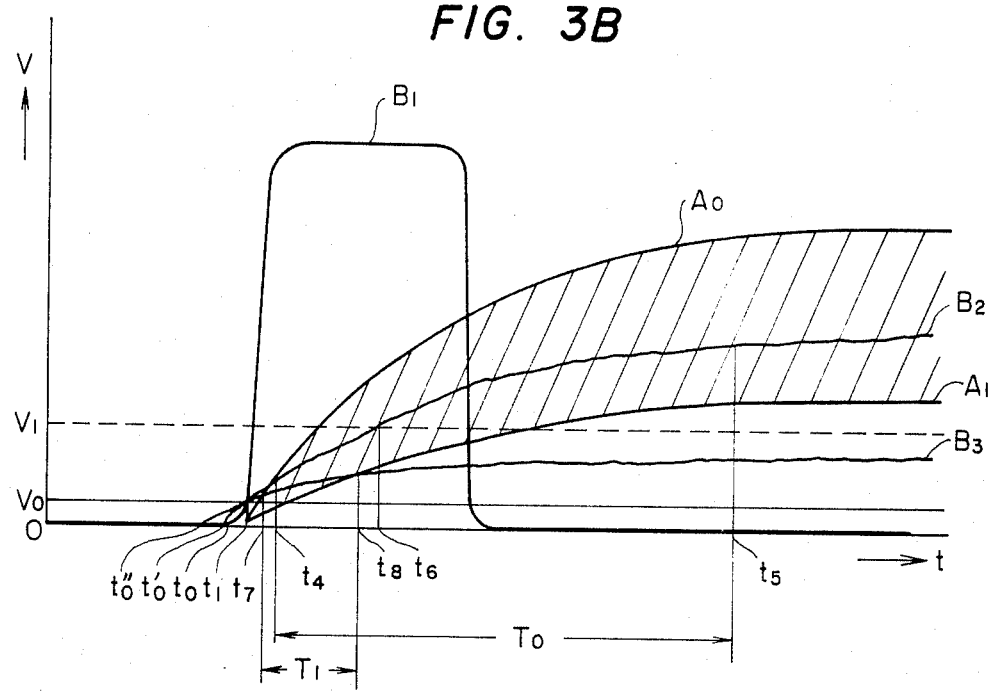

This difficulty may be overcome by increasing the operating voltage $V_0$ of the starting section 3 to a voltage $V_1$ as indicated by the broken line in FIG. 3B so that the operation is not effected for the smoke low in concentration. However, in this case, the newly determined operating voltage $V_1$ acts on the smoke of a fire, and accordingly the operation of the smoke detector is started at the time instant $t_6$ when the curve $B_2$ becomes higher than the operating voltage $V_1$. That is, the start of the operation of the smoke detector itself is later than the time instant $t_4$ when the signal comparison section 4 provides the output with the operating voltage $V_0$. This is undesirable for the smoke detector which is intended to detect a fire quickly and positively.

A smoke detector according to the second embodiment of this invention is made to detect the occurrence of fire with high accuracy. The smoke detector according to the second embodiment of this invention will be described with reference to FIGS. 2B, 3B and 4B.

Figure 2B:
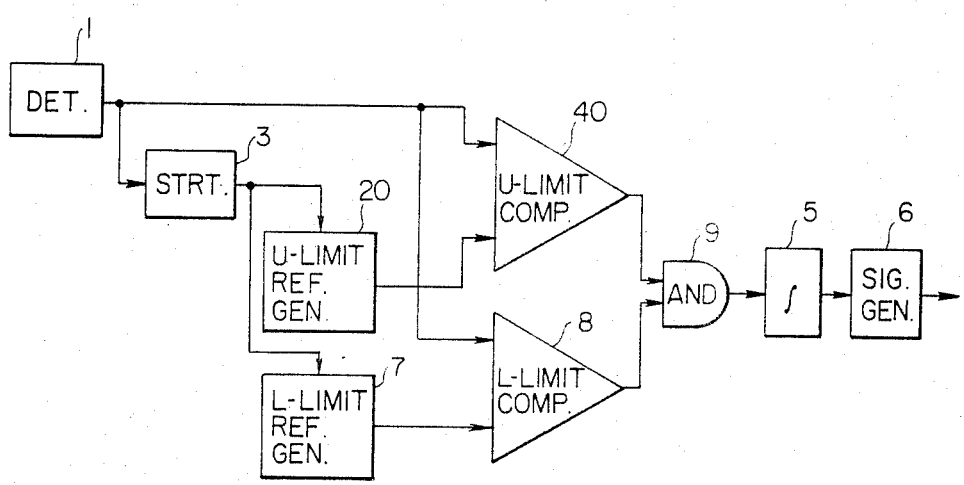

FIG. 2B is a block diagram outlining the arrangement of the smoke detector according to the second embodiment of the invention. The smoke detector includes the smoke detecting section 1, the starting section 3, the integrator 5 and the smoke sensing signal generating section 6 all of which are included in the smoke detector according to the first embodiment of the invention shown in FIG. 2A, an upper limit reference signal generating circuit 20 corresponding to the reference signal generating section 2 shown in FIG. 2A, an upper limit signal comparison section 40 corresponding to the signal comparison section 4 shown in FIG. 2A, a lower limit reference signal generating section 7 whose output varies with time according to a low-concentration smoke entering characteristic such as smoke from a cigarette, a lower limit signal comparison section 8 for providing an output when the detection signal becomes higher then the lower limit reference signal, and an AND gate circuit 9 which receives the outputs of the upper and lower limit signal comparison secitons 40 and 8 and applies the logical product of these outputs to the integrator 5.

The operation of the smoke detector thus constructed will be described in detal with reference to FIG. 3B which shows voltage variations under various conditions.

For the normal period of time during which neither smoke is produced nor insect enters into the detection chamber, the smoke detecting section 1 produces no detection signal while the reference signal generating sections 20 and 7 produce no reference signals, or the detection signal is slightly higher than the reference signals. Therefore, the upper limit signal comparison section 40 provides no output, and accordingly the AND gate circuit 9 provides no output.

When the entrance of an insect occurs and accordingly the detection signal of the smoke detecting section 1 changes abruptly as indicated in FIG. 3B by the curve $B_1$, the starting section 3 is operated at the time instant $t_1$ to start the reference signal generating sections 20 and 7. As a result, the upper limit reference signal generating section 20 produces a reference signal which rises with time according to the smoke entering characteristic of the smoke detecting section 1, as indicated by the curve $A_0$. At the same time, the lower limit reference signal generating section 7 produces a reference signal which rises with time according to the low-concentration smoke entering characteristic such as smoke from a cigarette, as indicated by the curve $A_1$, and which finally becomes a threshold signal for distinguishing smoke of a fire from smoke lower in concentration than that. As the curve $B_1$ is always higher in variation than the curve $A_0$, the upper limit signal comparison section 40 produces no output. However, since the curve $B_1$ becomes higher than the curve $A_1$, the lower limit signal comparison section 8 pruduces the output. As the output is interrupted by the AND gate circuit 9, no smoke sensing signal is produced.

In the case where smoke is produced by a fire at the time instant $t_0'$ and the voltage changes as indicated by the curve $B_2$, the starting section 3 is operated at the time instant $t_1$ to start the reference signal generating sections 20 and 7. As a result, similar to the above-described case, the reference signal generating sections 20 and 7 produce reference signals as indicated by the curves $A_0$ and $A_1$. In this case, the detection signal curve $B_2$ becomes lower than the upper limit reference signal curve $A_0$ from the time instant $t_4$, and is higher than the lower limit reference signal curve $A_1$. Therefore, the signal comparison sections 40 and 8 provide the outputs. The outputs are applied to the AND gate circuit 9 to enable the latter, the output of the AND gate circuit 9 is applied to the integrator 5, i.e., it is subjected to integration therein. When an integration value $T_0$ suitably preset is reached at the time instant $t_5$, the integrator 5 produces the output, so that the smoke sensing signal generating section 6 outputs the smoke sensing signal.

The specific features of the smoke detector according to the second embodiment of the invention reside in the following respects.

In the case where smoke low in concentration such as from a cigarette is produced at the time instant $t_0''$ and accordingly the voltage changes as indicated by the curve $B_3$, the starting section 3 is operated at the time instant $t_1$ to start the reference signal generating sections 20 and 7, as a result of which the reference signals are produced as indicated by the curves $A_0$ and $A_1$. In this case, at the time instant $t_7$ the detection signal curve $B_3$ becomes lower than the upper limit reference signal curve $A_0$, but is higher than the lower, limit reference signal curve $A_1$. As a result, the signal comparison sections 40 and 8 provide the outputs, which are applied to the AND gate circuit 9. The output of the AND gate circuit 9 is applied to the integrator 5. Since the lower limit reference signal curve $A_1$ is preset so that it is higher in variation than the detection signal curve $B_3$ of the low-concentration smoke, the detection signal curve $B_3$ becomes lower than the lower limit signal curve $A_1$ at the time instant $t_8$, whereupon the supply of the output of the lower signal comparison section 8 is stopped and therefore the output of the upper signal comparison section 40 is blocked by the AND gate circuit 9. Therefore, if, in this case, the value $T_0$ for the integrator 5 is set sufficiently longer than the period of time $T_1$ between the time instant $t_7$ and $t_8$, then no smoke sensing signal is produced.

Figure 4B:
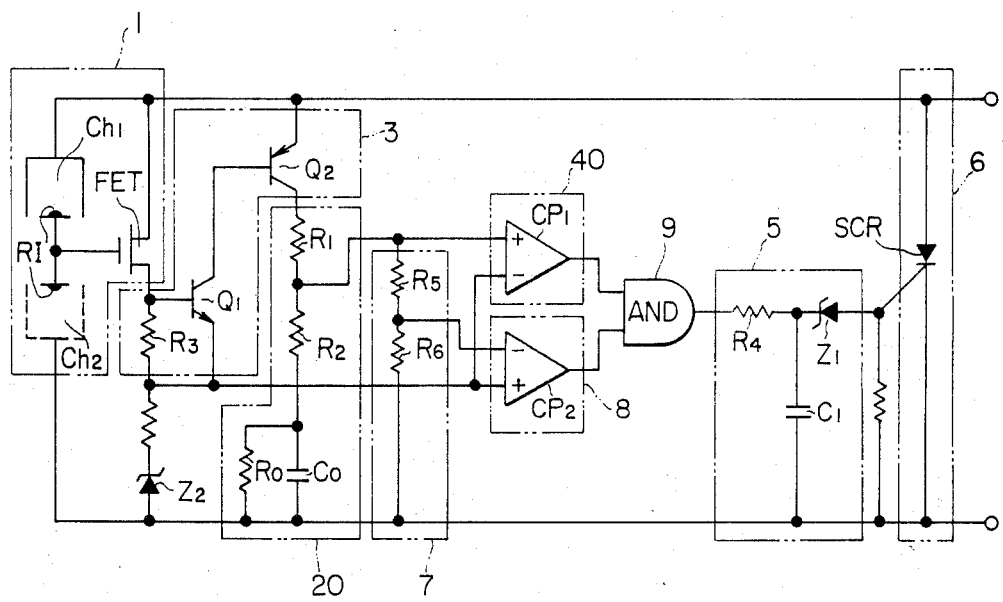

FIG. 4B shows a specific circuit diagram of the smoke detector according to the second embodiment of this invention, in which like reference numerals or like reference characters denote like elements or like sections shown in FIG. 4A. The upper limit reference signal generating section 20 is made up of a parallel circuit of a capacitor $C_0$ and a resistor $R_0$, and two resistors $R_1$ and $R_2$ which are connected in series to each other for regulating a current flowing in the parallel circuit and for dividing a signal voltage applied thereto. The lower limit reference signal generating section 7 includes two series-connected resistors $R_5$ and $R_6$ for subjecting the output signal of the section 20 to voltage division. The upper limit signal comparison section 40 is made up of a comparator $CP_1$, the inputs of which are connected to the upper limit reference signal generating seciton 20 and the smoke detecting section 1. The lower limit signal comparison section 8 is made up of a comparator $CP_2$, the inputs of which are connected to the lower limit reference signal generating section 7 and the smoke detecting section 1. The arrangements of smoke detecting section 1, starting section 3, integrator 5 and smoke sensing signal generating section 6 are identical to those shown in FIG. 4A, thus further description is unnecessary and is omitted herein.

In the smoke detector thus constructed, for the ordinary period of time during which no smoke is produced and no insect enters into the detection chamber, a low voltage signal is provided at the output side of the field-effect transistor FET in the smoke detecting section 1. However, since the voltage will never exceed the Zener voltage of the Zener diode $Z_2$ which determines the operating voltage of the starting section 3, no potential difference is developed across the resistor $R_3$ in the starting section 3. Therefore, the starting section 3 is not operated, and the reference signal generating section 20 and 7 are not driven. However, as the detection signal input side of the comparator $CP_2$, being applied with an ordinary level signal of the detection section 1, is higher than the lower limit reference signal input side of the comparator, the comparator $CP_2$ provides an output which is, however, blocked by the AND circuit 9.

When the production of smoke or the entry of an insect occurs, a detection signal, or a high voltage, is provided at the output of the smoke detecting section 1. This voltage is higher than the Zener voltage of the Zener diode $Z_2$, thus providing a current. Therefore, a potential difference is developed across the resistor $R_3$ in the starting section 3, so that the first transistor $Q_1$ is rendered conductive. At the same time, the second transistor $Q_2$ connected to the first transistor $Q_1$ is rendered conductive. Accordingly, the capacitor $C_0$ of upper limit reference signal generating section 20 is charged at a predetermined rate through two series connected resistors $R_1$ and $R_2$. As the potential of the capacitor $C_0$ is increased, the potential at the connection point of the resistors $R_1$ and $R_2$ is increased, thus providing an upper limit reference signal. In the lower limit signal generating section 7, the upper limit reference signal thus provided is subjected to voltage division by the resistors $R_5$ and $R_6$, and the potential at the voltage division point is increased, thus providing a lower limit reference signal. The reference signals which are increased and the detection signal are subjected to comparison in the comparators $CP_1$ and $CP_2$, respectively. If, in this case, the smoke is produced by a fire, then the detection signal is lower than the upper limit reference signal and higher than the lower limit reference signal. Therefore, the comparators $CP_1$ and $CP_2$ provide the outputs, which are applied to the AND gate circuit 9. The output of the AND gate circuit 9 is applied to the capacitor $C_1$ to charge the latter. When the voltage of the capacitor $C_1$ thus charged exceeds the Zener voltage of the Zener diode $Z_1$, a current flows in the gate electrode of the SCR, as a result of which the SCR is triggered to produce the smoke sensing signal.

In the case where smoke low in concentration such as from a cigarette is produced, the detection signal is lower than both of the reference signals. Accordingly, the comparator $CP_1$ in the upper limit signal comparison section 40 provides the output whereas the comaprator $CP_2$ in the lower limit signal comparison section 8 provides no output. Therefore, the AND gate circuit 9 is maintained closed, and no smoke sensing signal is provided.

In the case where the detection signal is provided by the entrance of an insect, the detection signal is higher than both of the reference signals. Accordingly, while the comparator $CP_2$ in the lower limit signal comaprison section 8 provides the output, the comparator $CP_1$ in the higher limit signal comparison section 40 provides no output. Therefore, the AND gate circuit 9 is maintained closed, and the SCR is not triggered.

As is apparent from the above description, the smoke detector of the second embodiment is simple in arrangement, and the detection signal due to the entrance of smoke resulting from a fire, the relatively moderate false detection signal due to the entry of cigarette smoke, and the relatively steep false detection signal due to the entrance of the insect can be accurately and quckly recognized according to the smoke entering characteristic of the detection chamber. Thus, a smoke detector low in manufacturing cost and high in performance can be provided according to the invention.

What is claimed is:

1. A smoke detector comprising:
   detection means for detecting smoke and providing a detection signal;
   reference signal generating means actuated in reponse to said detection signal for producing a reference signal which varies with time, said reference signal generating means comprising first reference signal generating means for generating a first reference signal and second reference signal generating means for generating a second reference signal which is lower than said first reference signal;
   comparison means for comparing said detection signal with said reference signal and producing a smoke implying output when said detection signal is lower than said reference signal, said comparison means comprising first comparison means for comparing said detection signal with said first reference signal and producing a first smoke implying output, and second comparison means for comparing said detection signal with said second reference signal and producing second smoke implying output; and
   AND gate means receiving said first and second smoke implying outputs.

2. The smoke detector as recited in claim 1 further comprising integration means connected to said AND gate means for subjecting an output of said AND gate means to integration, said integration means providing a trigger signal when an integration value of said integration means reaches a predetermined value.

3. The smoke detector as recited in claim 2 further comprising signal generating means for generating a smoke sensing signal in response to said trigger signal.

4. The smoke detector as recited in claim 1, 2 or 3, wherein said first and second reference signals vary with time.

5. The smoke detector as recited in claim 4 wherein said detection means comprises a detection chamber into which smoke is introduced, a reference chamber into which smoke is not substantially introduced, said detection chamber sand said reference chamber being connected in series to each other a first pair of electrodes provided in said detection chamber and a second pair of electrodes provided in said reference chamber, wherein said detection signal is derived from a connection point of said detection chamber and said reference chamber.

6. A smoke detector comprising:
   detection means for detecting smoke and providing a detection signal;
   reference signal generating means actuated in response to said detection signal for producing a reference signal which varies with time;
   comparison means for comparing said detection signal with said reference signal and producing a smoke implying output when said detection signal is lower than said reference signal; and
   an integration means connected to said comparison means for subjecting said smoke implying output to integration, said integration means providing a trigger signal when an integration value of said integration means reaches a pre-determined value.

7. The smoke detector as recited in claim 6 further comprising signal generating means for generating a smoke sensing signal in response to said trigger signal.

8. The smoke detector as recited in claim 1, 6, 2, 7, or 3, wherein said detection means comprises a detection chamber into which smoke is introduced, a reference chamber into which said smoke is not substantially introduced, said detection chamber and said reference chamber being connected in series to each other, a first pair of electrodes provided in said detection chamber and a second pair of electrodes provided in said reference chamber, wherein said detection signal is derived from a connection point of said detection chamber and said reference chamber.

* * * * *